United States Patent [19]

Bobbitt et al.

[11] Patent Number: 4,923,967
[45] Date of Patent: May 8, 1990

[54] PURIFICATION AND REFOLDING OF RECOMBINANT PROTEINS

[75] Inventors: Jesse L. Bobbitt; Joseph Manetta, both of Indianapolis, Ind.

[73] Assignee: Eli Lilly and Company, Indianapolis, Ind.

[21] Appl. No.: 248,757

[22] Filed: Sep. 26, 1988

[51] Int. Cl.$^5$ .................. C07K 3/24; C07K 15/06; C07K 7/40; C07K 13/00
[52] U.S. Cl. .................................. 530/351; 530/350; 530/399; 530/303; 530/418; 530/420; 530/427; 435/69.52
[58] Field of Search ............... 435/68, 183; 530/303, 530/350, 351, 399, 408, 418, 420, 421, 427, 404, 419

[56] References Cited

U.S. PATENT DOCUMENTS 4,569,790 2/1986 Koths et al. .................... 260/112 R
4,656,249 4/1987 Tregear et al. ...................... 530/324

FOREIGN PATENT DOCUMENTS

0111814A2 6/1984 European Pat. Off.
0156373A2 10/1985 European Pat. Off.
0208539A2 1/1987 European Pat. Off.

OTHER PUBLICATIONS

Tsugawa, R., Production of Recombinant Interleukin-2, Bio-Fair Tokyo '86.
Kato, K. et al., Purification and Characterization of Human Interleukin-2 Produced in *Escherichia coli*, Biochem. Biophys. Res. Comm. 130:692 (1985).
Weir, M. P., Purification and Renaturation of Recombinant Human Interleukin-2, Biochem. J. 245:85 (1987).
Furman, T. C., et al., Recombinant Human Insulin-Like Growth Factor II Expressed in *Escherichia coli*, Bio-Technology, 5:1047 (1987).
Weir, M. P., et al., Micropreparative Purification of Recombinant Human Interleukin-2, Journal of Chromatography, 396:209 (1987).
Tsuji, et al., Characterization of Disulfide Bonds in Inclusion Bodies and Its Oxidative Refolding, Biochemistry, 26:3129 (1987).

*Primary Examiner*—Margaret Moskowitz
*Assistant Examiner*—Keith C. Furman
*Attorney, Agent, or Firm*—Joseph A. Jones; Gerald V. Dahling; Leroy Whitaker

[57] ABSTRACT

The present invention discloses a new method for solubilizing and refolding recombinant proteins expressed as granules. The method involves sulfitolysis and the formation of a precipitate of protein-S-sulfonate by warming. The precipitate has been found to contain protein in high purity. In addition, proper folding takes place if the desired protein is fully reduced and passed through an intermediate concentration of denaturant which allows for a transition between its folded and unfolded states.

39 Claims, 13 Drawing Sheets

PURIFICATION AND REFOLDING OF RECOMBINANT PROTEINS

SUMMARY OF THE INVENTION

The present invention is a new process for obtaining high purity recombinant proteins in high yields. The process of the present invention is particularly advantageous because it eliminates the need for purification of recombinant protein by using conventional biological techniques such as HPLC (high performance liquid chromatography).

With the advent of recombinant DNA technology, the ability to amplify the amount of a specific protein produced by an organism has correspondingly led to increased expression of desired proteins. Such proteins, however, are usually expressed in granular, insoluble form. The granular form of an expressed recombinant protein is generally considered to be a function of high level expression and slow folding, resulting in the formation of insoluble, bioinactive aggregations of unfolded and/or partially folded proteins in the cell. This problem is particularly severe when proteins containing disulfide crosslinks (disulfide proteins) are expressed in bacteria, because after cell lysis the air oxidizes the mis-folded proteins which in turn leads to improper disulfide bonds and intermolecular cross-linking.

Because many recombinant proteins expressed in various organisms are expressed as insoluble granules, the ability to isolate and purify designated proteins from the granules is desired. The present invention addresses the problem of purification and discloses a new process for obtaining high yields of highly purified bioactive recombinant proteins, even when initially expressed as insoluble, bioinactive granules. In addition, the present invention also allows for the proper folding of recovered proteins. The importance of obtaining a properly folded protein lies in the fact that a protein is not biologically active until it is in its native folded conformation. While there are many factors that influence proper folding and while such factors may vary, the present invention provides a process for obtaining the proper folding of a wide variety of proteins using one standard procedure.

The present process involves protein sulfitolysis followed by a warming step which increases the temperature of the resultant protein-S-sulfonate, thereby allowing the protein-S-sulfonate to precipitate out in high purity. This precipitate is about 95% pure compared to the starting material. The precipitation of such highly charged protein-S-sulfonates was unexpected and, by obtaining such a high purity precipitate, eliminates the many conventional biological or biochemical purification techniques which would otherwise be required. In addition, by solubilizing and then reducing the protein or protein-S-sulfonate in a high concentration of denaturant followed by a lowering of the concentration by dilution or dialysis, the protein solution passes through a transition concentration at which proper folding takes place in high yields. Accordingly, as much as about 20% of the reduced protein refolds properly compared with only about 1% of proper protein folding when the present invention is not employed.

While common industrial procedures for purifying and refolding recombinant proteins, for example, as disclosed in U.S. Pat. No. 4,421,685, have included the use of S-sulfonated proteins, the present invention employs a heretofore unknown procedure for obtaining S-sulfonated protein as a precipitate, thereby allowing for recovery at high purity. After the sulfitolysis step is complete, the solution is solvent exchanged and the precipitate is obtained by warming the solvent exchanged solution of protein-S-sulfonate from a temperature of about 1°-6° C. to a temperature of about 18°-28° C. By obtaining such a high purity protein precipitate, the need to use conventional techniques, such as, for example, ion exchange chromatography, for further initial purification is eliminated.

The present invention is especially significant in that little is known about how or when a protein folds into its bioactive and correct configuration. (See Creighton, T. E., Proteins, W. H. Freeman and Co., N.Y., 1984. Heretofore, proper folding conditions were typically found empirically, requiring the development of costly tailor-made protocols for each recombinant protein that was to be refolded. The present invention solves this problem by providing a folding protocol which is applicable to virtually an recombinant protein produced in a microorganism. The present invention, therefore, eliminates the need for developing costly tailor-made purification and refolding protocols and thus increases the efficiency of producing recombinant proteins while reducing costs.

For purposes of the present invention, as disclosed and claimed herein, the following terms are as defined below.

Bioactive—The capacity for effecting an intended in vivo response.

Folding—The process whereby a protein is restored to a configuration that allows it to be stable and/or bioactive.

Granule—An aggregate of proteins containing a mixture of properly folded, partially folded, and/or unfolded proteins along with varying amounts of cellular impurities.

Recombinant DNA Cloning Vector—any selectable and autonomously replicating or chromosomally integrating agent, including but not limited to plasmids and phages, comprising a DNA molecule to which additional DNA can be or has been added.

Recombinant Protein—A protein expressed in a microorganism by virtue of the presence of a recombinant DNA vector.

Host Cell—A cell which has been or is capable of being transformed to express recombinant proteins.

Transformation—The introduction of DNA into a recipient host cell, including the viable protoplast thereof, that changes the genotype of the recipient cell.

Expression Vector—A recombinant DNA cloning vector designed in such a way that a foreign gene inserted into the vector will be expressed in the host organism.

DETAILED DESCRIPTION OF THE INVENTION

The present invention is a novel method for purifying recombinant proteins comprising:

(1) disrupting the cell wall of a host cell that contains insoluble cystaine-containing recombinant protein granules, said granules also containing cellular impurities, and isolating said granules from the cellular debris, (2) solubilizing said granules in a denaturing reagent containing a sulfitolyzing reagent to form a solution containing sulfitolyzed recombinant protein and said impurities, (3) solvent exchanging said solution containing sulfitolyzed recombinant protein and forming a precipitate of protein-S-sulfonate by raising the temperature of said solvent exchanged solution from a range of about 1° C. to about 6° C. to a range of about 18° C. to about 28° C., and, (4) isolating said protein precipitate from said impurities in the resultant supernatant.

The present invention further comprises a method for folding cysteine-containing recombinant proteins which comprises the additional steps:

(5) forming a solution of reduced protein by solubilizing said precipitate of step (4) in a denaturing reagent and then reducing by adding a reductant reagent; and, (6) diluting said solution of step (5) under conditions suitable for folding.

The present invention is best exemplified by the preparation of recombinant interleukin-2 (IL-2). This is accomplished by transforming a suitable host cell with a vector containing the IL-2 structural gene using conventional genetic engineering techniques. These conventional techniques include obtaining a gene that codes for the desired protein, inserting the gene into an appropriate expression vector in a position which permits expression of the gene, transforming competent host cells with the vector, identifying transformants, and culturing the transformants in a suitable growth medium. These conventional genetic engineering steps are well known in the art and are further disclosed in Maniatis, et al., 1982, Molecular Cloning (Cold Spring Harbor Laboratory).

Figure 13:
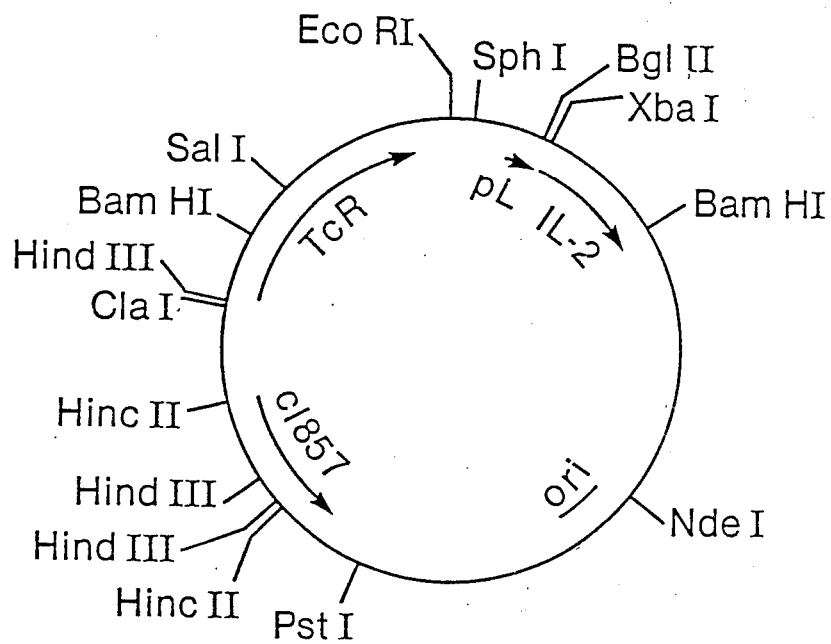
FIG. 13: Restriction site and Function Map of Plasmid pIL2365

The present invention is particularly useful for the preparation of recombinant proteins, such as IL-2. IL-2 is an immunomodulatory factor produced by certain subsets of T-lymphocytes that is responsible for promoting the proliferation of activated T-cells. The cloning of the IL-2 gene and its expression at high levels in *E. coli* has allowed for the production of large quantities of purified protein that is not contaminated by other natural lymphokines. As is the case with many other proteins, IL-2 can be expressed in *E. coli* in granular form and is thus particularly suited for purposes of the present invention. In the illustrative case of IL-2, expression was accomplished by transforming *E. coli* K12 RV308 with plasmid pIL2365. A detailed description of the construction of plasmid pIL2365 is presented below in Examples 1 through 10 and a restriction site map is presented in FIG. 13.

As is common in the production of recombinant proteins at high levels, the IL-2 expressed in *E. coli* takes the form of insoluble granules. The granules are prominent and so fill the cell that they are visible under light microscopy. The granules, after cell lysis, can be isolated by conventional techniques including filtration. The resultant isolated granules are then dissolved and sulfitolyzed in 4–6M guanidine·HCl. The IL-2-S-sulfonate can be identified by SDS (sodium dodecyl sulphate)-polyacrylamide gel electrophoresis or by HPLC, or any similar identification technique. After the sulfitolysis step is complete, the solution is solvent exchanged and the temperature is raised from about 1°–4° C. to about 18°–28° C., causing the desired product to settle out as a flocculent precipitate.

Obtaining a precipitate of such highly charged IL-2-S-sulfonate under these conditions was unexpected and allows one to obtain high purity IL-2 product without extensive early purification steps. Previous methods for purifying recombinant proteins have relied on standard techniques such as chromatography. These steps are both time consuming and costly. The purity of a denatured protein also effects the renaturation since the purer a denatured protein is, the better and more efficient the refolding reactions become. The above mentioned precipitation process can be modified and speeded up by adjusting the pH and adding ethanol and in other ways readily apparent to those skilled in the art.

Prior to the present invention, proper folding conditions for a particular protein were found empirically. The goal in any protein folding process is to effectively fold the protein not only by inc-easing the rate of the reaction, but also by using greater protein concentration without sacrificing yields. The in vivo conditions of pH, ionic strength, and ion concentrations on the ribosome (where the protein is synthesized) are certainly determining parameters for directing the folding process in vitro. In addition, every protein is believed to undergo a unique transition between its folded and unfolded state. By dissolving and reducing the present protein-S-sulfonate precipitate in a high concentration of denaturant followed by lowering the concentration by dilution with 10–100 mM Tris or dialysis, the protein solution passes through a transition concentration at which proper folding takes place in high yields. Therefore, despite the many parameters to which proper folding is sensitive, the method of the present invention may be used to achieve proper folding of virtually any protein.

The particular recombinant proteins which can be used for purposes of the present invention are not critical and may be generated by using established genetic engineering techniques. These conventional techniques include obtaining a gene that codes for a desired protein, inserting the gene into an appropriate expression vector in a position which permits expression of the gene, transforming competent host cells with the vector, identifying correct transformants, and culturing the transformants in a suitable growth medium. The choice of biological techniques and reagents used in the present invention is not of primary importance, but the high purity precipitate of the protein-S-sulfonate and the ability to properly refold a variety of proteins by on method is of great importance and one of the advantages of the present invention.

Those skilled in the art will realize that many of the genetic engineering techniques and reagents used in the present invention are not limited to those previously mentioned. For example, transformed cells can be ruptured and the desired granules freed by conventional mechanical methods, chemical methods or enzymatic methods. Mechanical methods may include, for example, sonication or homogenization. Chemical means may include lysis by alkali and enzymatic methods may include treatment with lysozyme. Any conventional method that frees the granules from the particular transformed host cells can be used. Once the cells are ruptured, the recovery of granules and removal of cellular debris may be achieved by a variety of conventional methods such as centrifugation and filtration. In addition, the particular reagents used with the 0.05-0.25M sodium sulfite to form the protein-S-sulfonate, as exemplified in Example 12, are not limited to the illustrative 1–10 mM sodium thiosulfate and 1–10 mM cysteine, but may also include 5–10 mM sodium tetrathionate and 0.1–1 mM copper sulfate. Skilled artisans will readily recognize that still other reagents can be used to obtain the desired result. Likewise, the denaturing reagents may include 6-8M urea, not just 4-6M guanidine·HCl. The denaturing reagent prevents refolding and crossfolding of the same protein molecule onto itself or two separate protein molecules onto each other. The only limitation is that the denaturant should not be so drastic so as to cause irreversible denaturation and irreversible loss of biological activity.

Skilled artisans will also recognize that solubilized protein may be identified not only by separating molecules based on their differential mobility in an electric field as in SDS-polyacrylamide gel electrophoresis but also by standard chromatography methods. The temperature for precipitation conditions may range from about 18°–28° C. with 25° C. being preferred. In addition, those skilled in the art will understand that the precipitate may be recovered not only by the production of high gravitational forces as in centrifugation but also by filtration methods. Likewise, reduction reactions are not limited to the use of 2–20 mM cysteine. Skilled artisans will recognize that 20–100 fold excess dithiothreitol, 20–100 fold excess mercaptoethanol and 2–20 mM glutathione may also be used. By way of illustration and not limitation, the following formula can be used for calculating the above-mentioned illustrative excess mercaptoethanol and dithiothreitol:

$$\text{mg reductant} = \frac{\text{mg IL-2 S—SO}_3}{15,500 \text{ gm/mole}} \times \frac{3^*}{1} \times \frac{20^{**}}{1} \times \frac{\text{molecular wt. of reductant}}{1}$$

*S—SO$_3$/molecule
**20 fold excess

Since the present method involves the precipitation of a protein S-sulfonate, the present method can only be used with proteins that contain cysteine. Cysteine is a sulphur-containing amino acid that contributes to the tertiary structure of proteins by forming disulfide bridges between cysteine molecules in close proximity. Many well known proteins form such disulfide bridges which are responsible for the protein's shape and biological activity. Human insulin, which consists of two polypeptide chains, A and B, linked by disulfide bridges between cysteine residues is one illustrative example. Human growth hormone (hGH) and bovine growth hormone (bGH) are two other proteins that contain cysteine. The present invention may also be used to purify and refold other recombinant products, such as, for example, human proinsulin, human insulin A chain, human insulin B chain, human insulin-like growth factor I (IGFI), human insulin-like growth factor II (IGFII), human tissue plasminogen activator, human interferon, mammalian protein, human protein and various other proteins of research and commercial value.

The recombinant proteins which can be used for purposes of the present invention may be generated by any number of established genetic engineering techniques. Several such techniques are described in Maniatis, et al., 1982, Molecular Cloning (Cold Spring Harbor Laboratory). Just as the present invention is not limited to purifying recombinant IL,-2 granules, the host cells useful in the present invention are not limited to E. coli. Host cells such as, for example, Bacillus, Streptomyces, yeast, and other organisms capable of being transformed and expressing proteins in granular form can also be used for purposes of the present invention.

The following examples further illustrate and provide detail but are in no way intended to limit the scope of the present invention. Both an explanation of and the actual procedures for constructing the invention are described where appropriate. Thus, Examples 1–10 describe the construction of plasmid pIL2365 via several plasmid intermediates while Examples 11–13 describe the conversion of insoluble IL-2 granules into properly folded protein. Unless otherwise stated in the examples, the reaction conditions, buffers, and protocols for conventional recombinant DNA procedures such as restriction enzyme digestion, DNA fragment isolation and purification, ligation, and transformation are as disclosed in Maniatis, et al., 1982, Molecular Cloning (Cold Spring, Harbor Laboratory), such disclosure being incorporated by reference herein. Plasmid pIL2365 codes for the expression of IL-2 at high levels in E. coli and is thus preferred for generating illustrative protein granule starting material. A flow diagram showing the construction of plasmid pIL2365 is presented in Table 1 below in outline form.

TABLE 1

Plasmid pIL2365 Construction Flow Diagram

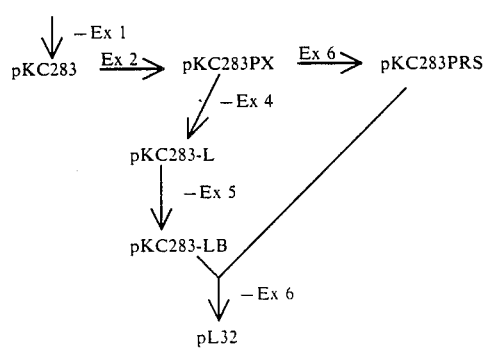

TABLE 1-continued
Plasmid pIL2365 Construction Flow Diagram

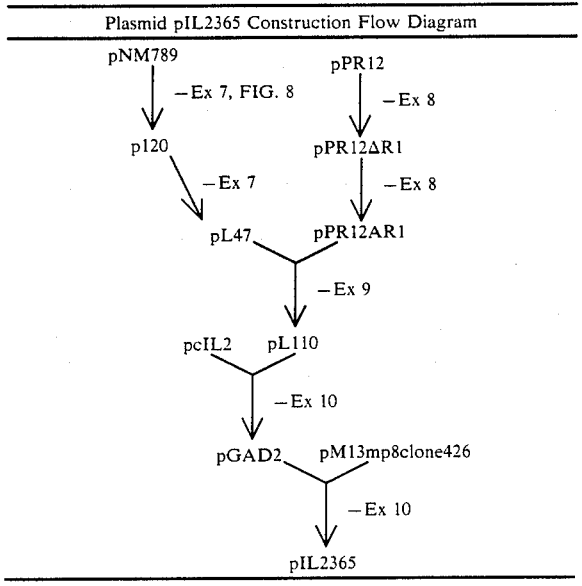

CONSTRUCTION OF PLASMID PIL2365 AND E. COLI K12 RV308/PIL2365

EXAMPLE 1

Isolation of Plasmid pKC283

Lyophils of *E. coli* K12 BE1201/pKC283 are obtained from the Northern Regional Research Laboratory, Peoria, Ill. 61604, under the accession number NRRL B-15830. The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 50 μg/ml in ampicillin and then incubated at 32° C. overnight. The *E. coli* K12 BE1201/pKC283 cells were cultured at 32° C., because the cells comprise a temperature-sensitive cI repressor gene integrated into the cellular DNA. When cells that comprise a wild-type lambda pL repressor gene rr do not comprise a lambda pL promoter are utilized in this plasmid isolation procedure, as described in subsequent Examples herein, the temperature of incubation is 37° C.

A small portion of the overnight culture is placed on LB-agar (LB medium with 15 g/l Bacto-agar) plates containing 50 g/ml ampicillin in a manner so as to obtain a single colony isolate of *E. coli* K12 BE1201/pKC283. The single colony obtained was inoculated into 10 ml of LB medium containing 50 μg/ml ampicillin and incubated overnight at 32° C. with vigorous shaking. The 10 ml overnight culture was inoculated into 500 ml LB medium containing 50 μg/ml ampicillin and incubated at 32° C. with vigorous shaking until the culture reached stationary phase.

The cells were harvested by centrifugation at 4000 g for 10 minutes at 4° C., and the supernatant was discarded. The cell pellet was washed in 100 ml of ice-cold STE buffer (0.1M NaCl; 10 mM Tris-HCl. pH 7.8; and 1 mM EDTA). After washing, the cell pellet was resuspended in 10 ml of Solution 1 (50 mM glucose; 25 mM Tris-HCl, pH 8.0; and 10 mM EDTA) containing 5 μg/ml lysozyme and left at room temperature for 10 minutes. Twenty ml of Solution 2 (0.2N NaOH and 1% SDS) were then added to the lysozyme-treated cells, and the solution was gently mixed by inversion. The mixture was incubated on ice for 10 minutes.

Fifteen ml of ice-cold 5M potassium acetate, pH 4.8, were added to the lysed-cell mixture and the solution mixed by inversion. The solution was incubated on ice for 10 minutes. The 5M potassium acetate solution was prepared by adding 11.5 ml of glacial acetic acid to 28.5 ml of water and 60 ml of 5M potassium acetate: the resulting solution is 3M with respect to potassium and 5M with respect to acetate.

The lysed cell mixture was centrifuged in a Beckman SW27 (or its equivalent) at 20,000 rpm for 20 minutes at 4° C. The cell DNA and debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer (10 mM Tris-HCl, pH 8.0, and 1 mM EDTA).

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentration was about 600 g/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a #21 hypodermic needle inserted through the side of the centrifuge tube.

Figure 1:
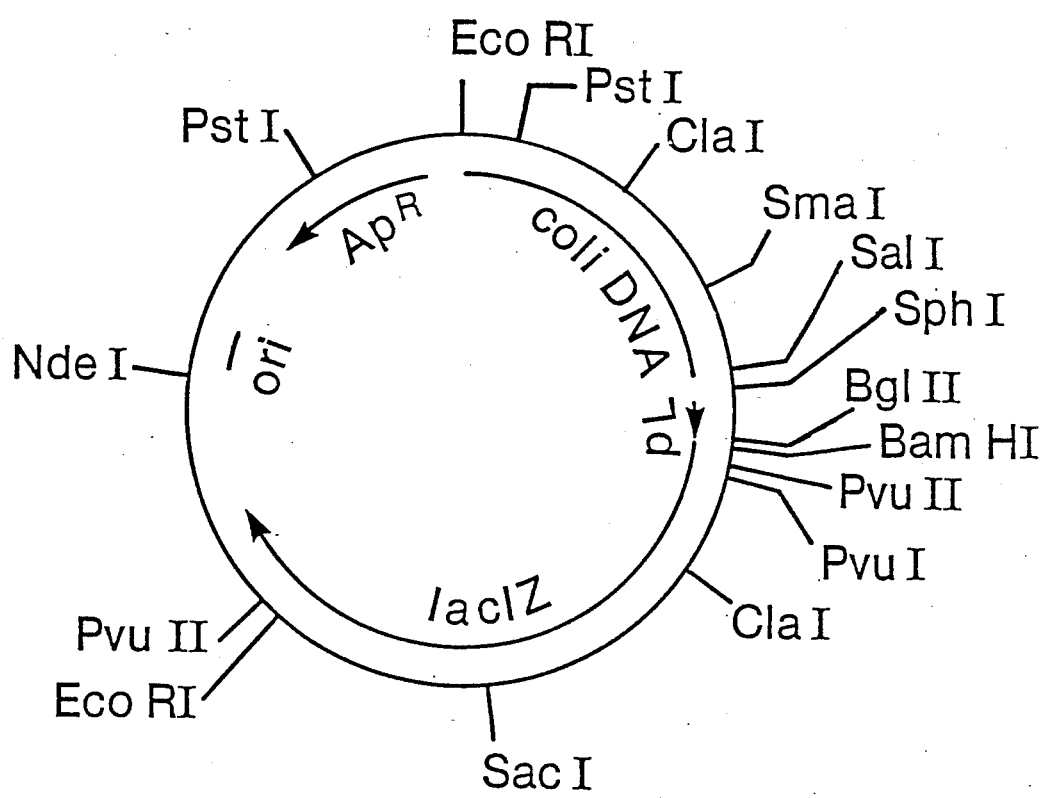
FIG. 1: Restriction site and Function Map of Plasmid pKC283

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pKC283 was obtained and stored at 4° C. in TE buffer at a concentration of about 1 μg/μl. A restriction site and function map of plasmid pKC283 is presented in FIG. 1 of the accompanying drawings.

EXAMPLE 2

Construction of Plasmid pKC283PX

About 10 μl of the plasmid pKC283 DNA prepared in Example 1 were mixed with 20 μl 10 X medium-salt restriction buffer (500 mM NaCl; 100 mM Tris-HCl, pH 7.5; 100 mM MgCl₂; and 10 mM DTT), 20 μl 1 mg/ml BSA, 5 μl restriction enzyme PvuII (~50 Units, as defined by Bethesda Research Laboratories (BRL), from which all restriction enzymes used herein were obtained), and 145 μl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 μl of TE buffer.

About 600 picomoles (pM) of XhoI linkers

were kinased in a mixture containing 10 μl 5 X Kinase Buffer (300 mM Tris-HCl, pH 7.8; 50 mM MgCl₂; and 25 mM DTT), 5 μl 5 mM ATP, 24 μl H₂O, 0.5 μl of T4 polynucleotide kinase (about 2.5 units as defined by P-L Biochemicals), 5 μl 1 mg/ml BSA, and 5 μl of 10 lmN spermidine by incubating the mixture at 37° C. for 30 minutes.

About 12.5 μl of the kinased XhoI linkars were added to the 5 μl of PvuII-digested plasmid pKC233 DNA, and then 2.5 μl of 10 X ligase buffer (300 mM Tris-HCl, pH 7.6; 100 mM MgCl₂; and 50 mM DTT), 2.5 μl of 1 mg/ml BSA, 7 μl of 5 mM ATP, 2.5 μl (about 2.5 units as defined by P-L Biochemicals) of T4 DNA ligase, 2.5 μl of 10 mM spermidine, and 3 μl of water were added &o the DNA. The resulting ligation reaction was incubated at 4° C. overnight. After the ligation reaction, the reaction mixture was adjusted to have the composition of high-salt buffer (0.1M NaCl; 0.05M Tris-HCl, pH 7.5; 10.0 mM MgCl₂; and 1 mM DTT). About 10 μl (100 units) of restriction enzyme XhoI were added to the mixture, and the resulting reaction was incubated at 37° C. for 2 hours.

Figure 2:
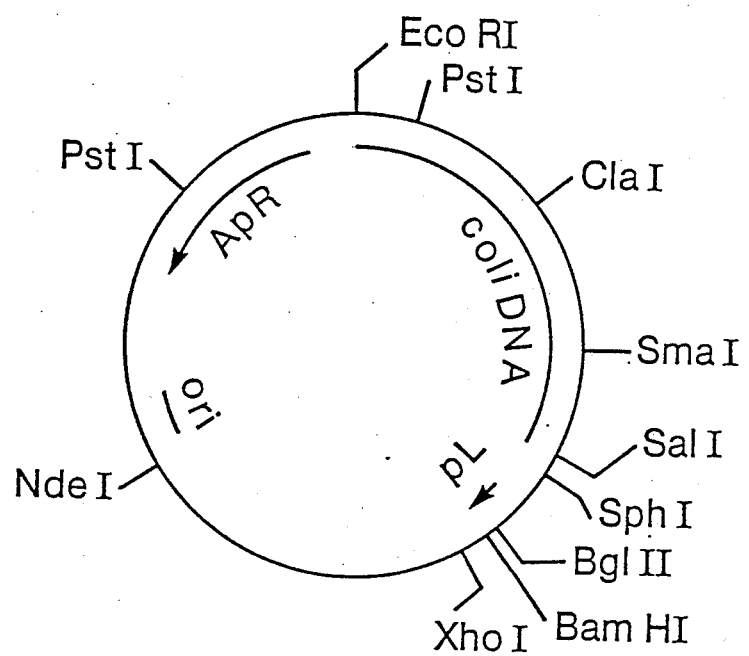
FIG. 2: Restriction site and Function Map of Plasmid pKC283PX

The reaction was terminated, and the XhoI-digested DNA was precipitated, resuspended, and ligated as described above, except that no XhoI linkers were added to the ligation mixture. The ligated DNA constituted the desired plasmid pKC283PX. A restriction site and function map of plasmid pKC283PX is presented in FIG. 2 of the accompanying drawings.

EXAMPLE 3

Construction of *E. coli* K12MO(λ+)/pKC283PX

*E. coli* K12 MO(λ+) can be obtained from the Northern Regional Research Laboratories in lyophylized form under the accession number NRRL B-15993. *E. coli* K12 MO(λ+) comprises the wild-type lambda pL cI repressor gene, so that transcription from the hybrid pL-lpp promoter does not occur in *E. coli* K12MO(λ+) cells. The lyophils are reconstituted, single colonies of MO(λ+) are isolated, and a 10 ml overnight culture of the MO(λ+) cells is prepared in substantial accordance with the procedure of Example 1, except that the temperature of incubation is 37° C. and no ampicillin is used in the growth media.

Fifty μl of the overnight culture were used to inoculate 5 ml of LB media which also contained 10 mM MgSO₄ and 10 mM MgCl₂. The culture was incubated at 37° C. for 16 hours with vigorous shaking. The culture was then diluted to 200 ml with LB media containing 10 mM MgSO₄ and 10 mM MgCl₂. The diluted culture was incubated at 37° C. with vigorous shaking until the absorbance at 550 nm (A₅₅₀) was about 0.5, which indicated a cell density of about 1×10⁸ cells/ml. The culture was cooled for ten minutes in an ice-water bath, and the cells were then collected by centrifugation at 4000 g for 10 minutes at 4° C. The cell pellet was resuspended in 100 ml of cold 10 mM MgSO₄ and then immediately re-pelleted by centrifugation. The cell pellet was resuspended in 100 ml of 30 mM CaCl₂ and incubated on ice for 20 minutes.

The cells were again collected by centrifugation and resuspended in 10 ml of 30 mM CaCl₂. A one-half ml aliquot of the cells was added to the ligated DNA prepared in Example 2; the DNA had been made 30 mM in CaCl₂. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred 1 aliquots were plated on LB-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 1, but the CsCl gradient step was omitted until the desired *E. coli* K12MO(λ+)/pKC283PX transformants were identified. A restriction site and function map of plasmid pKC283PX is presented in FIG. 2 of the accompanying drawings.

EXAMPLE 4

Construction of *E. coli* K12MO(λ+)/pKC283-L

Ten μg of plasmid pKC283PX DNA prepared in accordance with the procedure of Example 1 were dissolved in 20 μl of 10X high-salt buffer, 20 μl 1 mg/ml BSA, 5 μl (~50 units) restriction enzyme BglII, 5 μl (~50 units) restriction enzyme XhoI, and 150 μl of water, and the resulting reaction was incubated at 37° C. for two hours. The reaction was stopped, and after precipitating the BglII-XhoI digested DNA, the DNA was resuspended in 5 μl of TE buffer.

A DNA linker with single-stranded DNA ends characteristic of BglII and XhoI restriction enzyme cleavage was synthesized and kinased. The linker was kinased in substantial accordance with the procedure of Example 2. The DNA linker had the following structure:

The linker depicted above was synthesized from single-stranded deoxyoligonucleotides by procedures well known in the art. The single-stranded deoxyoligonucleotides can be synthesized with commercially available instruments, such as the 380A DNA Synthesizer marketed by Applied Biosystems (850 Lincoln Centre Drive, Foster City, Calif. 94404), which utilizes phosphoramidite chemistry. Other procedures for synthesizing DNA are also known in the art. The conventional modified phosphotriester method of synthesizing single stranded DNA is described in Itakura et al., 1977, Science 198:1056 and in Crea et al., 1978, Proc. Nat. Acad. Sci. U.S.A. 75:5765. In addition, an especially preferred method of synthesizing DNA is disclosed in Hsiung et al., 1983, Nucleic Acid Research 11:3227 and Narang et al., 1980, Methods in Enzymology 68:90.

Figure 3:
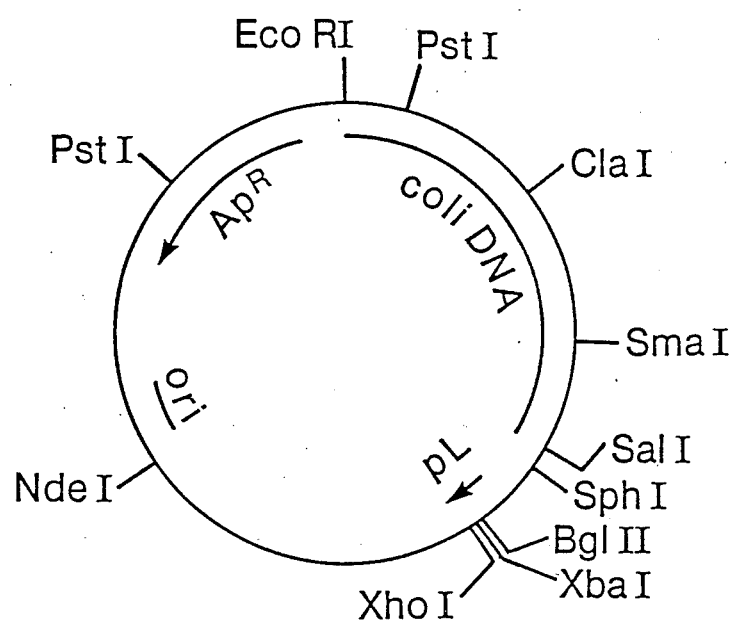
FIG. 3: Restriction site and Function Map of Plasmid pKC283-L

The linker and BglII-XhoI-digested plasmid pKC283PX were ligated in substantial accordance with the procedure of Example 2. The ligated DNA constituted the desired plasmid pKC283-L. A restriction site and function map of plasmid pKC283-L is presented in FIG. 3 of the accompanying drawings. The plasmid pKC283-L DNA was used to transform *E. coli* K12 MO(λ+) and the resulting *E. coli* K12

MO(λ+)/pKC283-L transformants were identified in substantial accordance with the procedure of Example 3.

EXAMPLE 5

Construction of *E. coli* K12 MO(λ+)/pKC283-LB

About 10 μg of plasmid pKC283-L DNA, prepared in substantial accordance with the procedures of Example 1, were dissolved in 20 μl 10X high-salt buffer, 20 μl 1 mg/ml BSA, 5 μl (~50 units) restriction enzyme XhoI, and 155 μl of H₂O, and the resulting reaction was incubated at 37° C. for two hours. The XhoI-digested plasmid pKC283-L DNA was then precipitated from the reaction mixture by the addition of three volumes of 95% ethanol and one-tenth volume of 3 M sodium acetate, incubation in a dry ice-ethanol bath for five minutes, and centrifugation. The resulting DNA pellet was washed with 70% ethanol, dried, and resuspended in 2 μl 10X nick-translation buffer (0.5 M Tris-HCl, pH 7.2; 0.1 M MgSO₄; and 1 mM DTT), 1 μl of a solution 2 mM in each of the deoxynucleotide triphosphates, 15 μl of H₂O, 1 μl (~6 units as defined by P-L Biochemicals) of Klenow, which is the large fragment of *E. coli* DNA polymerase I, and 1 μl of 1 mg/ml BSA. The resulting reaction was incubated at 25° C. for 30 minutes; the reaction was stopped by incubating the solution at 70° C. for five minutes.

BamHI linkers were kinased and ligated to the

XhoI-digested, Klenow-treated plasmid pKC283-L DNA in substantial accordance with the procedure of Example 2. After the ligation reaction, the DNA was digested with about 100 units of BamHI for about 2 hours at 37° C. in high-salt buffer. After the BamHI digestion, the DNA was prepared for ligation in substantial accordance with the procedure of Example 2.

Figure 4:
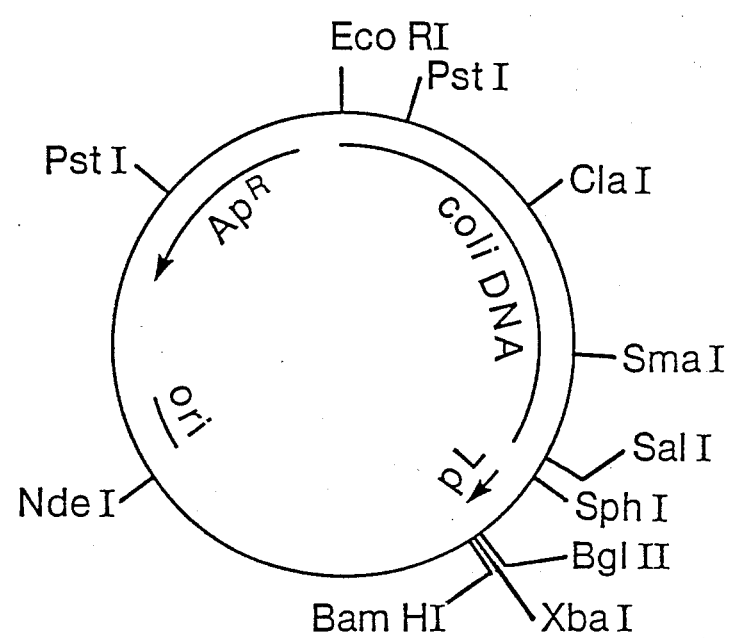
FIG. 4: Restriction site and Function Map of Plasmid pKC283-LB

The ~5.9 kb BamHI restriction fragment was circularized by ligation and transformed into *E. coli* K12 MO(λ+) in substantial accordance with the procedures of Examples 2 and 3. The *E. coli* K12 MO(λ+)/pKC283-LB transformants were identified, and then plasmid pKC283-LB DNA was prepared in substantial accordance with the procedure of Example 1. A restriction site and function map of plasmid pKC283-LB is presented in FIG. 4 of the accompanying drawings.

EXAMPLE 6

Construction of E. coli K12 MO(λ+)/pL32

About 10 μg of plasmid pKC283PX were digested with restriction enzyme SalI in high-salt buffer, treated with Klenow, and ligated to EcoRI linkers

Figure 5:
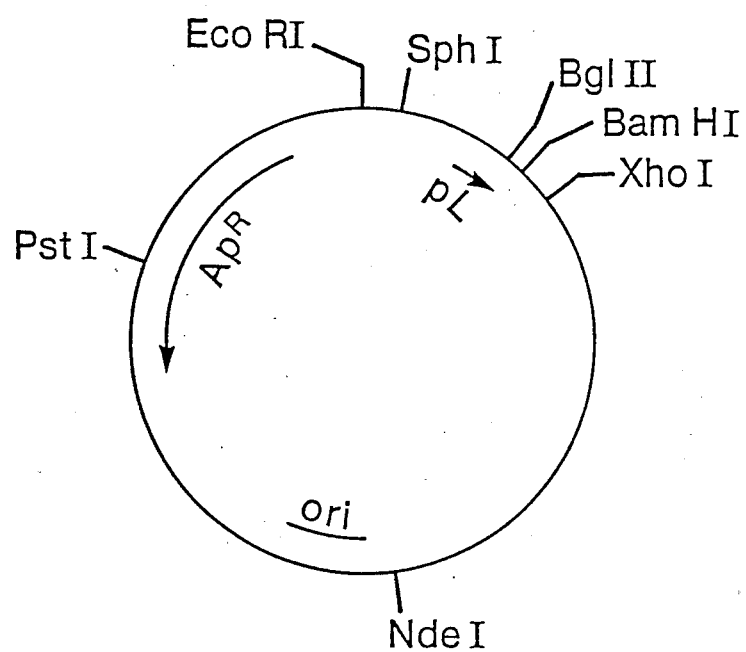
FIG. 5: Restriction site and Function Map of Plasmid pKC283PRS

in substantial accordance with the procedure of Example 5, with the exception of the starting plasmid, restriction enzymes, and linkers used. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform *E. coli* K12 MO(λ+) in substantial accordance with the procedure of Example 3. After the *E. coli* K12 MO(λ+)/pKC283PRS transformants were identified, plasmid pKC283PRS DNA was prepared in substantial accordance with the procedure of Example 1. A restriction site and function map of plasmid pKC283PRS is presented in FIG. 5 of the accompanying drawings.

About 10 μg of plasmid pKC283PRS were digested in 200 μl of high-salt buffer with about 50 units each of restriction enzymes PstI and SphI. After incubating the reaction at 37° C. for about 2 hours, the reaction mixture was electrophoresed on a 0.6% low-gelling-temperature agarose (FMC Corporation, Marine Colloids Division, Rockland, Me. 04841) gel for 2-3 hours at ~130 V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HCl, pH 7.6, was added to the tube containing the segment. The segment was then melted by incubation at 72° C. About 1 ug of the ~0.85 kb PstI-SphI restriction fragment of plasmid pKC283PRS was obtained in a volume of about 100 μl. In an analogous manner, plasmid pKC283-LB was digested with restriction enzymes PstI and SphI, and the resulting ~3.0 kb restriction fragment was isolated by agarose gel electrophoresis and prepared for ligation.

Figure 6:
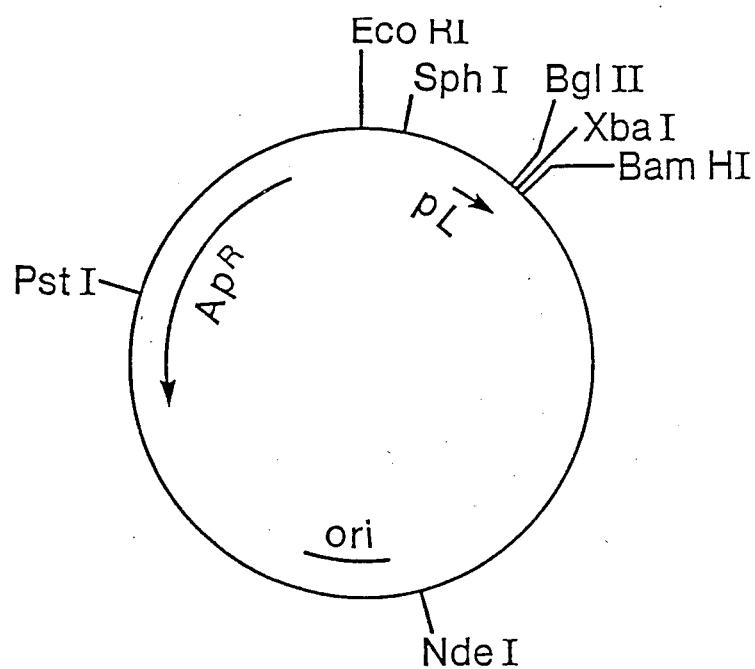
FIG. 6: Restriction site and Function Map of Plasmid pL32

The ~0.85 kb PstI-SphI restriction fragment of plasmid pKC283PRS was ligated to the ~3.0 kb PstI-SphI restriction fragment of plasmid pKC283-LB in substantial accordance with the procedure of Example 2. The ligated DNA constituted the desired plasmid pL32. A restriction site and function map of plasmid pL32 is presented in FIG. 6 of the accompanying drawings. Plasmid pL32 was transformed into *E. coli* K12 MO(λ+) cells in substantial accordance with the procedure of Example 3. Plasmid pL32 DNA was prepared from the *E. coli* K12 MO(λ+)/pL32 transformants in substantial accordance with the procedure of Example 1. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together. Alternatively, plasmid pL32 may be constructed by carrying out the SalI-EcoRI excision and ligation of the first paragraph of this Example upon plasmid pKC283-LB.

EXAMPLE 7

Construction of *E. coli* K12 MO(λ+)/pL47

Figure 7:
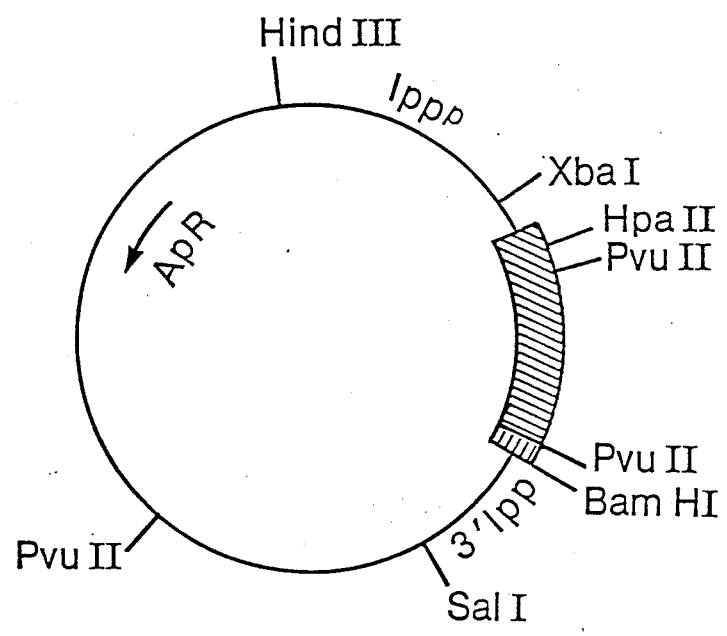
FIG. 7: Restriction site and Function Map of Plasmid pNM789
Figure 8:
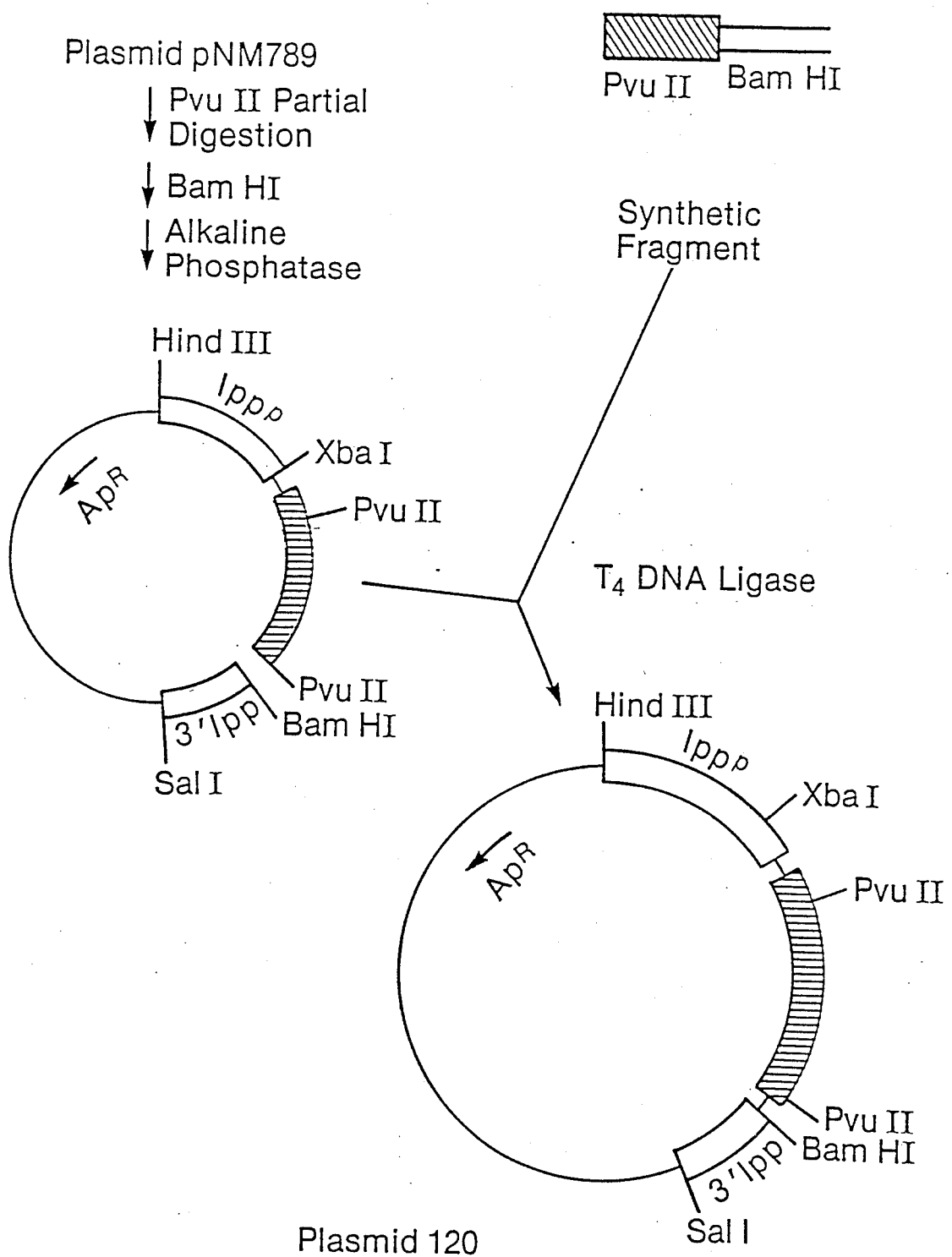
FIG. 8: Construction of Plasmid 120

*E. coli* K12 RV308/pNM789 can be obtained from the Northern Regional Research Laboratories in lyophylized form under the accession number NRRL B-18216. A restriction site and function map of pNM789 is presented in FIG. 7 of the accompanying drawings. Plasmid DNA is extracted from the culture in substantial accordance with the teaching of Example 1, except that the temperature of incubation is 37° C. Ten micrograms of pNM789 are suspended in 200 pl Pvull buffer (50 mM Tris-HCl (pH 7.5), 60 mM NaCl and 6mM MgCl₂) One unit of PvuII is added and the reaction mix is incubated for 5 minutes at 37° C. The enzyme is inactivated by heating 10 minutes at 65° C. 30 μl of 10× BamHI buffer (200 mM Tris-HCl (pH 8.0), 1M NaCl and 70 mM MgC₂), 70 μl H₂O and 10 units of BamHI are next added and the reaction is incubated for 1 hour at 37° C. This is followed by the addition of 5 units of alkaline phosphatase and incubation for 1 hour at 65° C. The DNA fragments are separated on a 1 percent agarose gel, and a DNA fragment (FIG. 8) the size of a single cut fragment is purified.

A DNA linker with a blunt end and a BamHI end is synthesized in substantial accordance with the teaching of Example 4. This linker (shown at 118 in FIG. 8) has the following structure:

The linker is kinased and ligated into the BamHI-PvuII digested plasmid pNM789 in substantial accordance with the teaching of Example 2. This ligation mixture is used to transform E. coli K12 RV308 cells and plasmid isolation is performed upon these transformants in substantial accordance with the teaching of Example 3. Several plasmids are selected which contain the appropriate size PvuII fragment (494bp) and XbaI-BamHI fragment (628bp). The sequence of at least two of these is determined by sequencing from the BamHI site toward the unique SmaI site and one clone is selected with the desired sequence. This intermediate plasmid is designated plasmid 120. A schematic outline of this procedure and a restriction site and function cap of plasmid 120 is presented in FIG. 8 of the accompanying drawings.

About 10 μg of plasmid 120 were then digested in 200 μl of high-salt buffer containing about 50 units each of restriction enzymes XbaI and BamHI. The digestion products were separated by agarose gel electrophoresis, and the ~0.6 kb XbaI-BamHI restriction fragment was isolated and prepared for ligation in substantial accordance with the procedure of Example 6.

Figure 9:
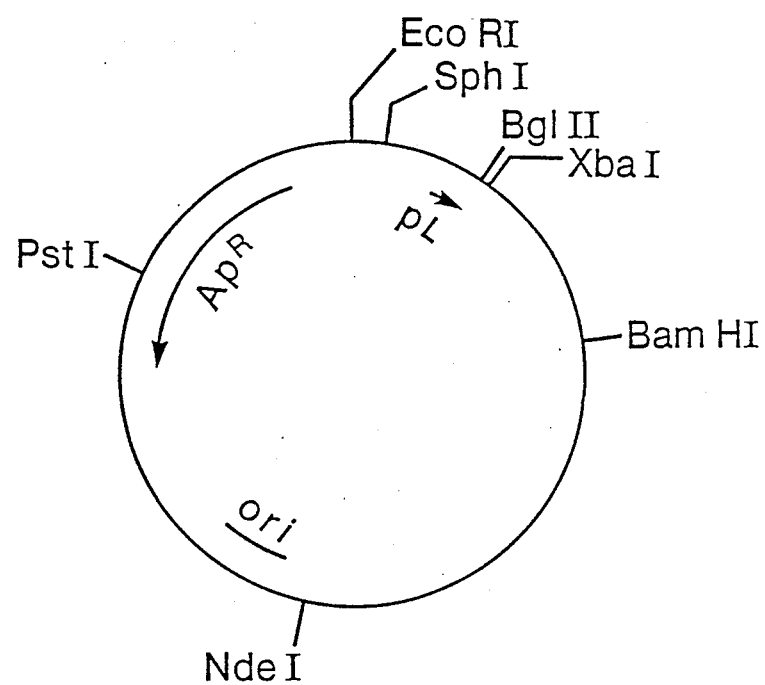
FIG. 9: Restriction site and Function Map of Plasmid pL47

Plasmid pL32 was also digested with restriction enzymes XbaI and BamHI, and the ~3.9 kb restriction fragment was isolated and prepared for ligation. The ~3.9 kb XbaI-BamH restriction fragment of plasmid pL32 was ligated to the ~0.6 kb XbaI-BamHI restriction fragment of plasmid 120 in substantial accordance with the procedure of Example 2 to yield plasmid pL47. A restriction site and function map of plasmid pL47 is presented in FIG. 9 of the accompanying drawings. Plasmid pL47 was transformed into E. coli K12 MO(λ+) in substantial accordance with the procedure of Example 3, and the E. coli K12 MO(λ+)/pL47 transformants were identified. Plasmid pL47 DNA was prepared from the transformants in substantial accordance with the procedures of Example 1.

EXAMPLE 8

Construction of E. coli K12 RV308/pPR12AR1

Figure 10:
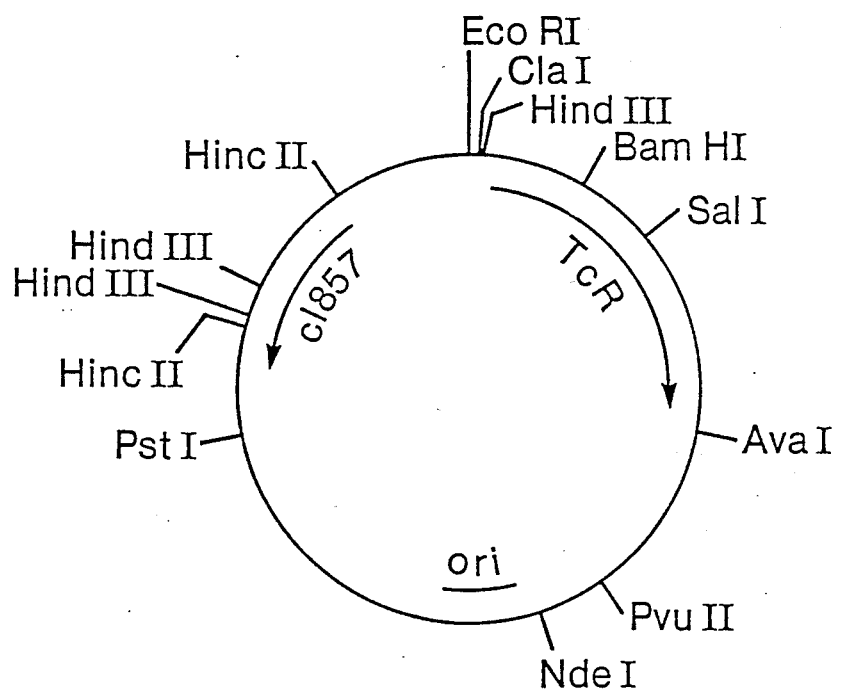
FIG. 10: Restriction site and Function Map of Plasmid pPR12

Plasmid pPR12 comprises the temperature sensitive pL repressor gene cI857 and the plasmid pBR322 tetracycline resistance-conferring gene. Plasmid pPR12 is disclosed and claimed in U.S. Pat. No. 4,436,815, issued Mar. 13, 1984. A restriction site and function map of plasmid pPR12 is presented in FIG. 10 of the accompanying drawings.

About 10 μg of plasmid pPR12 were digested with about 50 units of restriction enzyme EcoRI in 200 μl of high-salt buffer at 37° C. for two hours. The EcoRI-digested plasmid pPR12 DNA was precipitated and treated with Klenow in substantial accordance with the procedure of Example 5. After the Klenow reaction, the EcoRI-digested, Klenow-treated plasmid pPR12 DNA was recircularized by ligation in substantial accordance with the procedure of Example 2. The ligated DNA, which constituted the desired plasmid pPR12ΔR1, was used to transform E. coli K12 RV308 in substantial accordance with the procedure of Example 3, except that selection was based on tetracycline (5 ug/ml) resistance, not ampicillin resistance. E. coli K12 RV308 is available from the NRRL under the accession number NRRL B-15624. After the E. coli K12 RV308/pPR12ΔR1 transformants were identified, plasmid pPR12ΔR1 DNA was prepared from the transformants in substantial accordance with the procedure of Example 1.

About 10 μg of plasmid pPR12ΔR1 were digested with about 50 units of restriction enzyme AvaI in 200 μl of medium-salt buffer at 37° C. for 2 hours. The AvaI-digested plasmid pPR12ΔR1 DNA was precipitated and treated with Klenow in substantial accordance with the procedure of Example 5. After the Klenow reaction, the AvaI-digested, Klenow-treated plasmid pPR12ΔR1 DNA was ligated to EcoRI linkers

Figure 11:
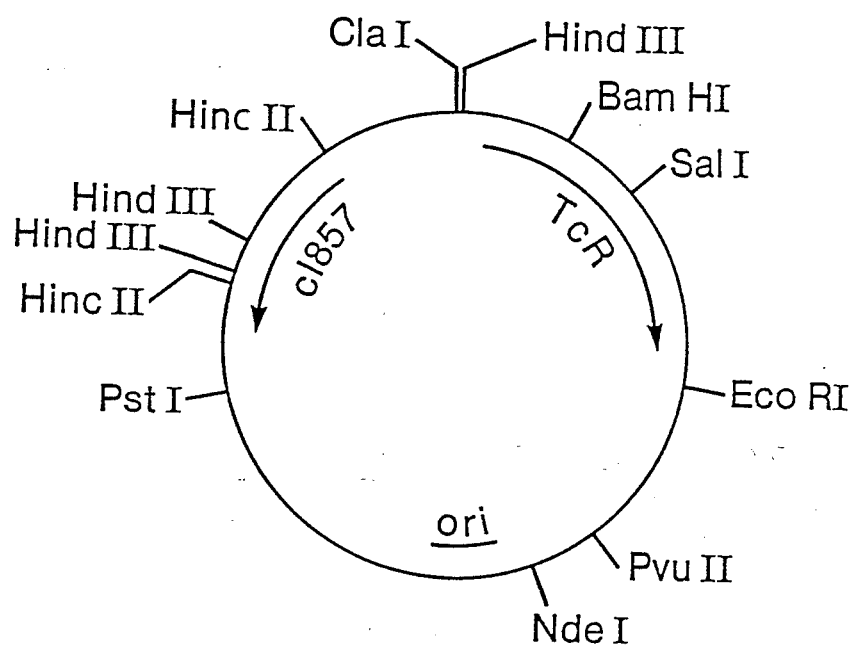
FIG. 11: Restriction site and Function Map of Plasmid pPR12AR1

in substantial accordance with the procedure of Example 2. After the linker ligation, the DNA was precipitated and then resuspended in about 200 μl of high-salt buffer containing about 50 units of restriction enzyme EcoRI. The resulting reaction was incubated at 37° C. for about 2 hours. After the EcoRI digestion, the reaction mixture was loaded onto an agarose gel, and the ~5.1 kb EcoRI restriction fragment was purified in substantial accordance with the procedure of Example 6. The ~5.1 kb EcoRI restriction fragment was recircularized by ligation in substantial accordance with the procedure of Example 2. The ligated DNA constituted the desired plasmid pPR12AR1. The plasmid pPR12AR1 DNA was transformed into E. coli K12 RV308 in substantial accordance with the procedure of Example 3, except that selection was based on tetracycline resistance, not ampicillin resistance. After identifying the E. coli K12 RV308,/pPR12AR1 transformants, plasmid pPR12AR1 DNA was prepared in substantial accordance with the procedure of Example 1. A restriction site and function map of plasmid pPR12AR1 is presented in FIG. 11 of the accompanying drawings.

EXAMPLE 9

Construction of E. coli K12 RV308/pL110

About 10 μg of plasmid pPR12AR1 DNA were suspended in about 200 ml of high-salt buffer containing about 50 units each of restriction enzymes PstI and EcoRI, and the digestion reaction was incubated at 37° C. for about 2 hours. The reaction mixture was then loaded onto an agarose gel, and the ~2.9 kb PstI-EcoRI restriction fragment of plasmid pPR12AR1 was isolated and prepared for ligation in substantial accordance with the procedure of Example 6.

About 10 ug of plasmid pL47 were digested with restriction enzymes PstI and BamHI in 200 μl of high-salt buffer at 37° C. for two hours. The PstI-BamHI-digested DNA was loaded onto an agarose gel, and the ~2.7 kb PstI-BamHI restriction fragment that comprised the origin of replication and a portion of the ampicillin resistance-conferring gene was isolated and prepared for ligation in substantial accordance with the procedure of Example 6. In a separate reaction about 10 ug of plasmid pL47 DNA were digested with restriction enzymes EcoRI and BamHI in 200 μl of high-salt buffer at 37° C. for two hours, and the ~1.03 kb EcoRI-BamHI restriction fragment was isolated and prepared for ligation in substantial accordance with the procedure of Example 6. The ~2 μg of the ~1.03 kb EcoRI-BamHI restriction fragment obtained were used in the construction of plasmid pL110.

Figure 12:
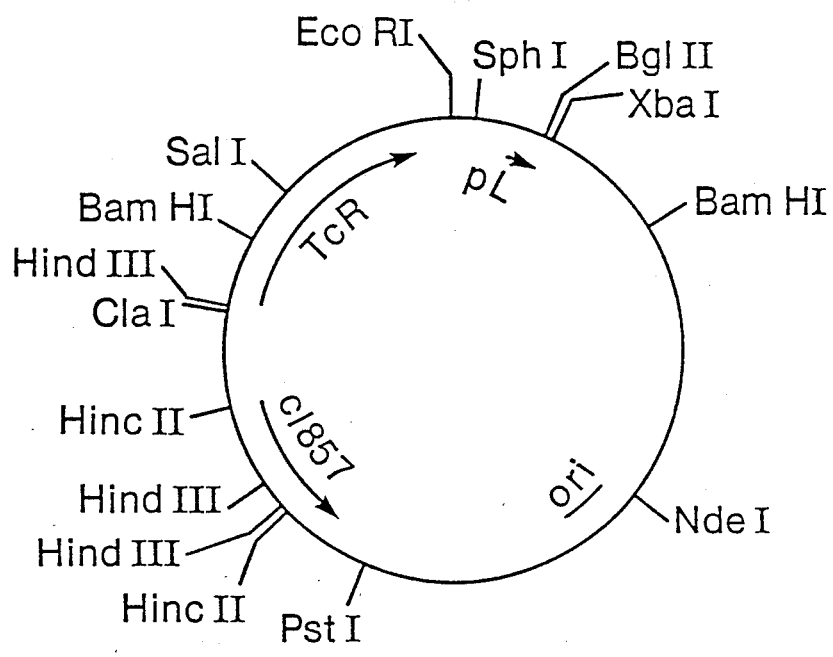
FIG. 12: Restriction site and Function Map of Plasmid pL110

The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to construct plasmid pL110, and the agitated DNA was used to transform *E. coli* K12RV308 in substantial accordance with the procedure of Examples 2 and 3, except that tetracycline resistance, not ampicillin resistance, was used as the basis for selecting transformants. A restriction site and function map of plasmid pL110 is presented in FIG. 12 of the accompanying drawings.

EXAMPLE 10

Construction of Plasmid pIL2365

Plasmid cIL-2 (NRRL B-18381) contains the cDNA fragment coding for the signal peptide and the N-terminal 100 residues of mature IL-2.

About 5 μg of plasmid cIL-2 DNA isolated in substantial accordance with the teaching of Example 1, was digested with 5 units (units, as defined by Bethesda Research Laboratories, from which all restriction enzymes used herein were obtained) of HgiAI and 5 units of PstI restriction enzymes and 5 μl of 10× standard restriction buffer (50 mM NaCl, 10 mM Tris-Cl (pH 7.5), 10mM MgCl$_2$, 1 mM dithiothreitol), hereinafter medium salt buffer. The approximately 291 base pair IL-2 fragment was isolated and purified by electrophoresis on a polyacrylamide gel.

The IL-2 fragment was then given blunt ends by adding 2 units T4 polymerase and digesting with 5 units of Sau3A restriction enzyme in medium salt buffer. The blunt ended IL-2 fragment was then ligated to the synthetic linker

```
5'-GATCTTAAAAAGGGTATCGACCATGGCACCT-3'
   ||||||||||||||||||||||||||||||
    AATTTTTCCCATAGCTGGTACCGTGGA
``` by adding about 1 μg of kinased linkers and 200 ng of the IL-2 fragment and incubating the resulting mixture at 4° C. for 20 hours. Next, the sequence was digested with 5 units BglII and 5 units Sau3A restriction enzyme in medium salt buffer and the resulting fragment was ligated into vector pL110 (which had previously been digested with 4 units BglII restriction enzyme and partially digested with 2 units BamHI restriction enzyme, again in medium salt restriction buffer).

The resultant plasmid, pGAD2, was then partially digested, as described above, with 2 units BamHI restriction enzyme. Next, plasmid pM13mp8clone426 (NRRL-B-18380), isolated in substantial accordance with the teaching of Example 1, was digested, as disclosed above, with restriction enzyme Sau3A. A 242 base pair Sau3A fragment coding for the C-terminal 33 residues of IL-2 was then conventionally isolated and ligated into the partially digested pGAD2 resulting in plasmid pIL2365. Plasmid pIL2365, which contains the entire coding sequence for IL-2 operably positioned for expression, was then used to transform *E. coli* K2 RV308 (NRRL B-15624) in substantial accordance with the teaching of Example 3. The resultant transformants were conventionally cultured for production of IL-2 in the form of insoluble granules. A restriction site and function map of plasmid pIL2365 is presented in FIG. 13 of the accompanying drawings.

EXAMPLE 11

Isolation of Interleukin-2 (IL-2) Granules

About 300 grams of wet, packed, *E. coli* K12 RV308/pIL2365 cells were suspended in 2400 ml. 0.05M Tris-HCl (pH 8.0) and lysed by the addition of 1.2 grams lysozyme (Sigma Grade III) in 300 ml. 0.05M EDTA (ethylene-diamine tetraacetic acid). The cells were dispersed by stirring and then the viscous DNA was sheared by brief sonication. When lysis was complete (judged by microscopic examination after one hour), 600 grams DEAE (diethyl amino ethyl) cellulose (Whatman DE52) were added while stirring. The suspension was then filtered, with the turbid filtrate containing the desired granules of IL-2. The filter cake was washed with 3000 ml. of the Tris-HCl buffer (pH 8.0) until the wash was clear and the combined filtrate and wash was centrifuged at 10,000× g. for 30 minutes. After centrifugation the collected precipitate was washed successively with 30% acetonitrile in Tris-HCl buffer, 1M KCl, and water. The resultant washed granules were then suspended in 1 liter of water. The yield of protein granules as determined by the biuret method (See Colowick, S.P., and N. O. Kaplan, editors. Methods In Enzymology, Vol. 3, pp. 450-451. Academic Press, New York; 1957) was 5.5 grams. The granule preparation was frozen at −20° C. for future use.

EXAMPLE 12

Preparation of IL-2-S-Sulfonate

About 5.5 grams of granules from Example 11 were dissolved in 500 ml. 6M guanidine·HCl (Gu-HCl). To the 500 ml. were added 0.1M sodium sulfite (6.3 gm.), 0.05M Tris (3.03 gm.), 0.005M sodium thiosulfate (620 mg.), 0.005M cysteine (303 mg.), and 50 μl. of a 1×10$^{-3}$M CuSO$_4$ soln. After the pH was adjusted to 7.8, the sulfitolysis was conducted at about 4° C. for 48 hours with stirring. The resultant mixture was clarified by centrifugation and then solvent exchanged into 7M urea, 0.1M Tris (pH 8.5), and 0.1M sodium sulfite, on a 10 liter column of Sephadex G-75 (Pharmacia, Piscataway, N.J. 08554-9932). The column effluent was monitored by absorption at 280 nm, and the peak containing the IL-2-S-sulfonate was identified by SDS-polyacrylamide gel electrophoresis. The G-75 column also separated a peak of high molecular weight protein. The fraction containing the IL-2-S-sulfonate was allowed to warm to about 25° C., and the desired product settled out as a flocculent precipitate. Optionally, the precipitation process can be speeded up by lowering the pH to 7.5 with HCl and adding ethanol to 10%. The desired IL-2-S-sulfonate precipitate was recovered by centrifugation and washed twice with water, yielding about 1.3 grams.

EXAMPLE 13

Solubilizing and Folding of IL-2

About 40 mg of IL-2 S-SO$_3$ precipitate, obtained in Example 12, was dissolved at 4° C. into about 66.7 ml of 6M Gu-HCl, 80.7 mg cysteine and 3.2 mg cystine. The pH was then adjusted to 8 by the addition of solid Tris. While constantly stirring the solution, a total of 200 ml of cold water was pumped in at 1.6 ml/min. The solution was then covered and allowed to incubate at 4° C. overnight. Next, the solution was dialyzed in a Spectra-Por #1 (Spectrum Medical Industries, Inc., Los Angeles, Calif. 90054) against 4L of 0.05M Tris (pH 9.0) for four hours and then dialized overnight with fresh Tris. The insoluble material was removed by centrifugation and then discarded out 1.5 ml of acetic acid was then added to solution, the solution was concentrated on an Amicon YM-5 membrane (Amicon, Danvers, Mass.) to about 10 ml and passed over a Sephadex G-75 Column equilibrated with 0.1M sodium acetate buffer pH 4.5, to remove any aggregated protein. The resultant refolded IL-2 was finally concentrated on a YM-5 membrane and stored frozen at −20° C. Proper refolding was verified by chromatography on a reversed phase C-4 HPLC column (Vydac, Hesperia, Calif. 92345). The resultant IL-2 was biologically active as determined by its ability to cause proliferator of the IL-2 dependent cell line CTLL-2, available from the American Type Culture Collection (ATCC), Rockville, Md., 20852, under the accession number TIB214.

We claim:

1. A method for purifying recombinant human Interleukin-2 comprising:
   (a) disrupting the cell wall of a host cell that contains insoluble recombinant Interluekin-2 granules, said granules also containing cellular impurities, and isolating said granules from the cellular debris;
   (b) solubilizing said granules in a denaturing reagent containing a sulfitolyzing reagent to form a solution containing sulfitolyzed recombinant human Interleukin-2 and said impurities;
   (c) solvent exchanging said solution containing sulfitolyzed recombinant human Interleukin-2 into a solution comprising approximately 7M urea at a temperature in the range of about 1° C. to about 6° C. and forming a precipitate of said sulfitolyzed recombinant Interleukin-2 by raising the temperatures of said solvent exchanged solution from a range of about 1° C. to 6° C. to a range of about 18° C. to about 28° C. and
   (d) isolating said recombinant human Interleukin-2 sulfitolyzed precipitate from said impurities in the resultant supernatant.

2. The method of claim 1 wherein the denaturing reagent is selected from the group consisting of guanidine hydrochloride and urea.

3. The method of claim 2 wherein the denaturing reagent is about 4–6M guanidine hydrochloride.

4. The method of claim 3 wherein the denaturing reagent is about 6M guanidine hydrochloride.

5. The method of claim 2 wherein the denaturing reagent is about 6–8M urea.

6. The method of claim 5 wherein the denaturing reagent is about 7M urea.

7. The method of claim 1 wherein the sulfitolyzing reagent comprises sodium sulfite and a member selected from the group consisting of sodium thiosulfate, cysteine, sodium tetrathionate, and copper sulfate.

8. The method of claim 7 wherein the sodium sulfite has a concentration of about 25–250mM.

9. The method of claim 8 wherein the sodium sulfite has a concentration of about 100mM.

10. The method of claim 7 wherein the sulfitolyzing reagent comprises sodium sulfite and about 2–20 mM cysteine.

11. The method of claim 10 wherein the sulfitolyzing reagent comprises about 0.1M sodium sulfite and about 5 mM cysteine.

12. The method of claim 7 wherein the sulfitolyzing reagent comprises sodium sulfite and about 5–10 mM sodium tetrathionate.

13. The method of claim 12 wherein the sulfitolyzing reagent comprises 100 mM sodium sulfite and about 10 mM sodium tetrathionate.

14. The method of claim 7 wherein the sulfitolyzing reagent comprises sodium sulfite and about 1–10 mM sodium thiosulfate.

15. The method of claim 14 wherein the sulfitolyzing reagent comprises about 100 mM sodium sulfite and about 5 mM sodium thiosulfate.

16. The method of claim 7 wherein the sulfitolyzing reagent comprises sodium sulfite and about 0.1–1 mM copper sulfate.

17. The method of claim 16 wherein the sulfitolyzing reagent comprises about 100 mM sodium sulfite and about 0.5 mM copper sulfate.

18. The method of claim 1 wherein the temperature in step (c) is raised to about 25° C.

19. The method of claim 1 wherein the sulfitolyzing reagent comprises along 0.1M sodium sulfite, the denaturing reagent is about 6M guanidine hydrochloride, the solvent is exchanged into a solution comprising about 7M urea, 0.1M Tris(hydroxymethyl)-aminomethane (pH 8.5) and 0.1M sodium sulfite, and the temperature in step (c) is raised to about 25° C.

20. A method for folding recombinant human Interleukin-2 comprising:
   (a) isolating the Interleukin-2-S-sulfonate precipitate obtained from the method of claim 1;
   (b) forming a solution of reduced Interleukin-2 by solubilizing said precipitate of step (a) in a denaturing reagent and then reducing by adding a reductant reagent; and
   (c) diluting said solution of step (b) under conditions suitable for folding.

21. The method of claim 20 wherein the denaturing reagent is selected from the group consisting of urea and guanidine hydrochloride.

22. The method of claim 21 wherein the denaturing reagent is about 4–6M guanidine hydrochloride.

23. The method of claim 21 wherein the denaturing reagent is about 6M guanidine hydrochloride.

24. The method of claim 21 wherein the denaturing reagent is about 6–8M urea.

25. The method of claim 24 wherein the denaturing reagent is about 7M urea.

26. The method of claim 20 wherein said solution of step (b) is diluted in step (c) by changing concentration of guanidine hydrochloride from about 6M to about 1.5M.

27. The method of claim 26 wherein the concentration of said solution is changed by the addition of about 10–100 mM Tris(hydroxymethyl)-aminomethane.

28. The method of claim 27 wherein the concentration of Tris(hydroxymethyl)-aminomethane is about 10 mM.

29. The method of claim 20 wherein the reductant reagent is selected from the group consisting of mercaptoethanol, cysteine, glutathione and dithiothreitol.

30. The method of claim 29 wherein the reductant reagent is about 10-100 fold excess mercaptoethanol.

31. The method of claim 30 wherein the reductant reagent is about 20 fold excess mercaptoethanol.

32. The method of claim 29 wherein the reductant reagent is about 2-20 mM cysteine.

33. The method of claim 32 wherein the reductant reagent is about 10 mM cysteine.

34. The method of claim 29 wherein the reductant reagent is about 2-20 mM glutathione.

35. The method of claim 34 wherein the reductant reagent is about 10 mM glutathione.

36. The method of claim 29 wherein the reductant reagent is about 20-100 fold excess dithiothreitol.

37. The method of claim 36 wherein the reductant reagent is about 20 fold excess dithiothreitol.

38. The method of claim 20 wherein the denaturing reagent is about 6M guanidine hydrochloride, the reductant reagent is about 0.01M cysteine, and said solution of step (b) is diluted by changing the concentration from about 6M guanidine hydrochloride to about 1.5M guanidine hydrochloride by the addition of about 0.01M Tris(hydroxymethyl)-aminomethane.

39. A method for purifying an folding recombinant human Interleukin-2 comprising:
(a) disrupting the cell wall of a host cell that contains insoluble recombinant human Interleukin-2 granules, said granules also containing cellular impurities, and isolating said granules from the cellular debris,
(b) solubilizing said granules in about 6M guanidine hydrochloride and a sulfitolyzing reagent comprising about 0.1M sodium sulfite to form a solution containing sulfitolyzed Interleukin-2 protein;
(c) solvent exchanging said solution containing sulfitolyzed Interleukin-2 protein into a solution comprising about 7M urea, 0.1M Tris(hydroxymethyl)-aminomethane (pH 8.5), and 0.1M sodium sulfite, at a temperature in the range of about 1° C. to about 6° C., and forming a precipitate of the Interleukin-2-sulfonate by raising the temperature of said solvent exchanged solution to about 25° C.;
(d) forming a solution of reduced protein by solubilizing and reducing 40 mg of said Interleukin-2-S-sulfonate precipitate at 0.6 mg/ml in a solution comprising about 6M guanidine hydrochloride, 80 mg cysteine and 3 mg cysteine;
(e) changing the concentration of said solution of step (d) from about 6M guanidine hydrochloride to about 1.5M guanidine hydrochloride by adding sufficient 0.01M Tris(hydroxymethyl)-aminomethane.

* * * * *